United States Patent [19]
Weiss

[11] Patent Number: 5,134,538
[45] Date of Patent: * Jul. 28, 1992

[54] ADJUSTABLE, CONDUCTIVE BODY STRAP

[75] Inventor: John W. Weiss, St. Paul, Minn.

[73] Assignee: Minnesota Mining and Manufacturing Company, St. Paul, Minn.

[*] Notice: The portion of the term of this patent subsequent to Jan. 19, 2005 has been disclaimed.

[21] Appl. No.: 329,508

[22] Filed: Mar. 27, 1989

Related U.S. Application Data

[63] Continuation-in-part of Ser. No. 134,819, Dec. 18, 1987, Pat. No. 4,816,964, and a continuation-in-part of Ser. No. 134,820, Dec. 18, 1987, Pat. No. 4,845,505, which is a continuation-in-part of Ser. No. 37,616, Apr. 13, 1987, Pat. No. 4,720,765.

[51] Int. Cl.$^5$ .................. H05F 3/02; A44B 11/06
[52] U.S. Cl. .................. 361/220; 361/212; 439/37; 24/188; 24/265 BC
[58] Field of Search .............. 361/212, 220, 223, 232; 307/326, 327; 174/5 SB, 5 SG; 2/321; 24/170, 188, 265 WS, 265 BC; 57/901; 439/37; 24/191, 193, 198, 169, 519, 265 C

[56] References Cited

U.S. PATENT DOCUMENTS

| 4,577,256 | 3/1986 | Breidegam | 361/220 |
| 4,596,053 | 6/1986 | Cohen et al. | 2/1 |
| 4,662,695 | 5/1987 | Gordon et al. | 361/220 X |
| 4,670,945 | 6/1987 | Banks | 24/170 |
| 4,674,155 | 6/1987 | Turtle et al. | 24/170 |
| 4,676,561 | 6/1987 | Barrett, II | 439/37 |
| 4,720,765 | 1/1988 | Weiss | 361/220 |
| 4,816,964 | 3/1989 | Weiss | 361/220 |
| 4,845,585 | 7/1989 | Weiss | 361/220 |

OTHER PUBLICATIONS

Desco Technical Bulletin; P-2005 Jun. 1987; Desco Industries, Inc. 761 Penarth Ave., Walnut Calif. 91789.

Primary Examiner—Todd E. DeBoer
Assistant Examiner—David Osborn
Attorney, Agent, or Firm—Gary L. Griswold; Walter N. Kirn; William D. Bauer

[57] ABSTRACT

An adjustable, conductive body strap utilizing a connector securing a strip of material held in a closed loop with a mechanical connector with the interior surface of the strip of material being electrically conductive. An electrical connector connects the conductive surface of the strip of material to a connection point to provide for external electrical ground connection. The mechanical connector secures one end of the strip of material in place. The mechanical connector adjustably secures the opposite end of the strip of material.

5 Claims, 4 Drawing Sheets

ADJUSTABLE, CONDUCTIVE BODY STRAP

RELATED APPLICATIONS

The present application is a continuation-in-part of U.S. Ser. No. 07/134,819, John Walter Weiss, Adjustable, Conductive Body Strap, filed Dec. 18, 1987, now U.S. Pat. No. 4,816,964, issued Mar. 28, 1989, and of U.S. Ser. No. 07/134,820, John Walter Weiss, Adjustable, Conductive Body Strap, filed Dec. 18, 1987 now U.S. Pat. No. 4,845,585 issued Jul. 4, 1989; both of which are a continuation-in-part of U.S. Ser. No. 07/037,616, John Waiter Weiss, Adjustable, Conductive, Body Strap, filed Apr. 13, 1987, now U.S. Pat. No. 4,720,765, issued Jan. 19, 1988.

BACKGROUND OF THE INVENTION

The present invention relates generally to electrically conductive body straps and more particularly to electrically conductive body straps which are adjustable.

The build-up of electrostatic charges and their subsequent discharge is a significant problem in certain industries. Individuals working in an everyday work environment commonly may develop thousands of volts of electrostatic charge potential by, as an example, walking across carpeting or moving dissimilar objects against each other. An individual, or object, so charged presents a severe hazard in contain environments. One example is an explosive environment where the danger is inherently obvious. Another example is the electronic integrated circuit (component) industry. The charged individual or object may discharge near or through an electrostatic sensitive electronic component. For example, an individual who is electrostatically charged may hold an electrostatic sensitive component and then lay the component on a surface, e.g., a grounded work surface, at a different potential from the the individual. At the instant of contact, a potential difference of thousands of volts may exist across the component, from the electrostatically charged individual to the grounded work surface. The current passing through or near, due to the electric field generated, may damage the component. The damage caused to the component may cause it to fail immediately or, worse, could degrade the operating characteristics or the reliability of the component. The result is either expensive rework or, worse, the existence of substandard or unreliable equipment in the field.

A device which is used to help control the electrostatic charge build-up on a person is a body strap or wrist strap to be worn by the individual. The body straps are conductive on the surface contacting the skin surface and provide for an electrical connection point. An electrical ground cord may then be connected to the strap connecting the strap to an electrical ground potential, preferably through a predetermined limiting resistance usually built into the connector or the cord itself. So connected, such a body strap operates by draining any accumulated electrostatic charge on the individual to ground before the electrostatic charge build-up reaches dangerous levels.

One prior art body strap is described in U.S. Pat. No. 4,398,277, Christiansen et al, Conductive Elastomeric Body Strap, which is hereby incorporated by reference. Christiansen et al describes a body strap which is constructed from a band of fabric formed into a closed loop to encircle a body part, e.g., wrist, to which it is to be connected. The fabric is electrically conductive on the interior surface of the closed loop contacting the skin. A mechanical connection mechanism holds the loop of fabric in a fixed predetermined size. An electrical connection mechanism provides for an electrical connection between the conductive inner surface of the fabric to an electrical grounding cord which may be attached to the strap. The fabric is elastomeric to enable the body strap to expand to slip over the hand and still be snug around the wrist.

In the body strap described in Christiansen et al, the opposite ends of the fabric are permanently secured in the mechanical connector. The body of the connector has projections which grip the fabric and hold the fabric in the connector when the cover is secured. Thus, the resultant body strap formed is a fixed closed loop size. Since the fabric has a limit on the degree of its elastic nature, a range of sizes of closed loops for the body strap must be provided. This results in the necessity of stocking a plurality of differing sizes of body straps. Further, the elastomeric characteristics of the fabric generally means a fixed "life" of use of the fabric before its elastomeric or electroconductivity characteristics begin to break down. Since the fabric is secured in the connector at the factory, the replacement of the fabric requires replacement of the entire body strap. The ends of projections 32 in Christiansen et al are sonically welded after the fabric is in place to "mushroom" the ends of the projections in order to ensure that the fabric is secured in the connector.

The Charge-Guard 2200 series of static control wrist straps manufactured by Minnesota Mining and Manufacturing Company, St. Paul, Minn. is constructed generally as described in Christiansen et al (Charge-Guard is a registered trademark of Minnesota Mining and Manufacturing Company, St. Paul, Minn.).

U.S. Pat. No. 4,577,256, Breidegam, Woven Stretchable Grounding Strap, describes a wrist strap designed to be used to control electrostatic charge accumulations. The Breidegam strap has a clasp which allows its size to be adjusted. The adjustable clasp avoids the need to manufacture two or more models of the strap for different sized wrists. This does require that the strap be individually adjusted to fit snugly around the wrist of the individual wearer. If inadvertently or intentionally maladjusted, proper electrostatic protection may not be achieved. In the Breidegam strap, one end of the fabric is permanently secured into the clasp and held by plate and a rivet. Thus, one end of the fabric is fixed at the factory for the entire life of the strap. The second end of the fabric is engaged in the clasp by a pivotally mounted gate which when closed "jams" the fabric holding it in place, optionally with teeth to help the securing of the fabric. Typically, a pivotally mounted "jam" or "wedge" as is described in Breidegam is referred to as an "over-center" device. These devices operate by wedging the fabric between the jam member and a reaction member by using an eccentric pivot with a relatively long jam operating lever to gain the necessary leverage for the jam to work. One problem in a strap as described in Breidegam is that it does not allow for full 360 degree electrical continuity because the fabric is electrically only connected at one end. Since electrical contact is only provided to the external ground cord from the one fixed end of the fabric, any charge contacting the inner surface of the fabric must travel around the strap in one direction only until reaching the fixed end. This requires, in some instances, that a charge must follow only one path to travel almost entirely around the fabric before being connected to a ground strap. Since the electrical conductivity of the fabric, due to its elasticity, is typically the weakest link in a wrist strap grounding system, along with the fabric to skin contact, such one way only conductivity is a serious problem. Another problem with the Breidegam strap is that the pivotal mounted gate does not lend itself to economical manufacture. Because of the forces involved, the pivot points are required to be quite sturdily built.

A problem with prior art wrist straps is that of contamination of electronic "clean rooms" with material from the wrist strap itself. Since wrist straps are employed to protect sensitive electronic circuitry and may be employed in electronic "clean rooms" in which extremely sensitive electronic integrated circuits or electronic assembly is performed, it is indeed ironic that wrist straps intended to protect those operations from harmful electrostatic discharge could actually cause harm to those very operations due to contamination. Since the fabric making up the strip of material forming the loop is composed of many fibers, when the fabric is cut, small "ends" of these fibers may become loose, fall from the wrist and become unwanted contaminates. This problem is especially troublesome with some of these wrist straps since sizing the wrist strap to a particular person's wrist involves pulling some of the fabric out of the mechanical connector holding the fabric in place. The excess of this fabric is then sometimes cut off resulting in a new end of material which is ripe for contaminates.

SUMMARY OF THE INVENTION

The present invention provides a body or wrist strap useful for the control of electrostatic charge accumulation. The body strap provides adjustability without the use of expensive "over-center" jam mechanisms. The body strap provides full 360 degree electrical continuity around the body strap having two parallel paths to ground, provides easy readily readjustable sizing by the individual user or users and, because no free end of the fabric is exposed the possibility of having the electrically conductive inner surface of the fabric exposed is eliminated.

Thus, the present invention provides an adjustable, conductive body strap. The body strap has a strip of material having a first end and a second end, with the strip of material being electrically conductive on at least one surface, being elastomerically extensible in its longitudinal direction, and being of at least a length to enable the strip of material to encircle a body part. The body strap also has an electrically insulative outer piece and an electrically conductive inner piece. The outer piece and the inner piece are secured together to form a mechanical connector receiving the first end and the second end of the strip of material to form a closed loop with the strip of material with the at least one surface toward the interior of the closed loop. The mechanical connector receives the first end of the strip of material from a first direction with the end of the strip of material being secured therein. The electrically conductive inner piece having a portion around which the second end of the strip of material is passed. The electrically conductive inner piece makes electrical contact with the at least one surface of the first end of the strip of material and also makes electrical contact with the at least one surface of the strip of material where the strip of material passes around the portion providing 360 degree electrical continuity. An adjustment mechanism is secured to the second end of the strip of material and to the strip of material intermediate the mechanical connector adjustably holding the strip of material in the closed loop. An electrical connection mechanism is coupled to the strip of material making electrical contact with the at least one conductive surface and providing a connection point for an electrical cable capable of connecting the conductive body strap to ground.

The present invention also provides an adjustable, conductive body strap. The body strap has a strip of material having a first end and a second end. The strip of material is electrically conductive on at least one surface, is elastomerically extensible in its longitudinal direction, and is of at least a length to enable the strip of material to encircle a body part. A mechanical connector receives the first end and the second end of the strip of material to form a closed loop with the strip of material with the at least one surface toward the interior of the closed loop. The mechanical connector has a first part receiving the first end of the strip of material from a first direction with the end of the strip of material being secured therein and having a second part receiving the second end of the strip of material. The second part of the mechanical connector has a plate over which the second end of the strip of material is passed. The plate has a plurality of spikes upon which the strip of material may be impaled after the strip of material has been pulled tight around the body part. The second part of the mechanical connector further has a hinged cover capable of being secured over the spikes of the plate trapping the strip of material thereon. A second cover is secured to the first part of the mechanical connector. An electrical connection mechanism is coupled to the strip of material making electrical contact with the at least one conductive surface and providing a connection point for an electrical cable capable of connecting the conductive body strap to ground.

The present invention also provides an adjustable, conductive body strap. The body strap has a strip of material having a first end and a second end. The strip of material is electrically conductive on at least one surface, is elastomerically extensible in its longitudinal direction, and is of at least a length to enable the strip of material to encircle a body part. A mechanical connector receives the first end and the second end of the strip of material to form a closed loop with the strip of material with the at least one surface toward the interior of the closed loop. The mechanical connector has a first part receiving the first end of the strip of material from a first direction with the end of the strip of material being secured therein and has a second part receiving the second end of the strip of material. The second part of the mechanical connector has a transverse bar around which the second end of the strip of material is passed passing firstly interior of the transverse bar and secondly exterior of the transverse bar. The transverse bar has a plurality of spikes mounted on its exterior surface upon which the strip of material may be impaled after the strip of material has been pulled tight around the body part. The second part of the mechanical connector further has a hinged cover for being secured over the spikes of the transverse bar trapping the strip of material thereon. An electrical connection mechanism is coupled to the strip of material for making electrical contact with the at least one conductive surface and for providing a connection point for an electrical cable capable of connecting the conductive body strap to ground.

Preferably, the body straps of the present invention have fabric ends which are fused following cutting at the factory to prevent contaminates from the fabric being introduced into the electronic work place.

BRIEF DESCRIPTION OF THE DRAWINGS

The foregoing advantages, construction and operation of the present invention will become more readily apparent from the following drawings and accompanying description in which.

DESCRIPTION OF THE PREFERRED EMBODIMENTS

Figure 1:
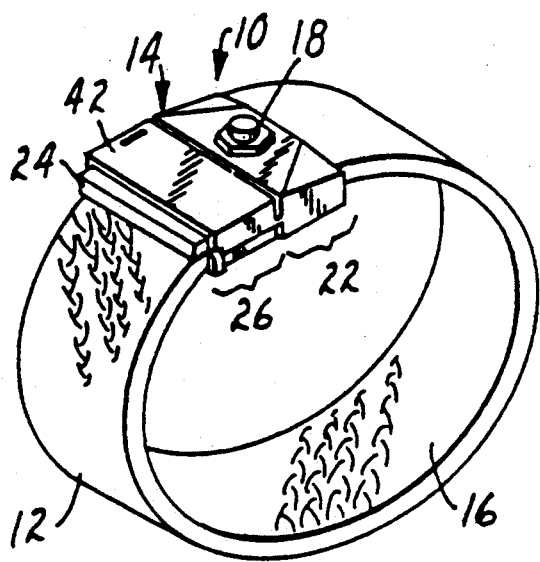
FIG. 1 illustrates an isometric view of an embodiment of the body strap of the present invention.

An embodiment of the adjustable, electrically conductive body strap 10 is illustrated in FIG. 1. The body strap 10 is formed into a closed loop designed to fit snugly around a portion of the body, e.g., a wrist or an ankle. The loop is formed by a strip of material 12 formed into a loop by connector 14. Connector 14 forms both the mechanical connection holding both ends of the strip of material 12 and the electrical connection mechanism providing a point for external connection of the body strap 10 to a ground potential. The interior surface 16 of the strip of material 12 is electrically conductive and should intimately contact the skin of the individual wearer of the body strap 10 when it is in position. Thus, electrostatic charges accumulating on the person of the wearer can be transported from the skin of the wearer to the conductive interior surface 16 of the body strap 10 transported to connector 14 and made available for conduction to ground through provision for connecting a grounding cord such as cord connector 18. Strip of material 12 may be formed of any suitable elastomeric electrically conductive material such as a fabric to form the band portion of the body strap 10. In a preferred embodiment, strip of material 12 is a knit fabric containing both elastomeric and electrically conductive fibers as desribed in Christiansen et al. Optionally, however, strip of material 12 could also be constructed from a stretch weave material such as is described in Breidegam. A first end 20 of the strip of material 12 is mechanically secured in a first part 22 of connector 14. The second end 24 of the strip of material 12 is adjustably secured in a second part 26 of connector 14.

Figure 4:
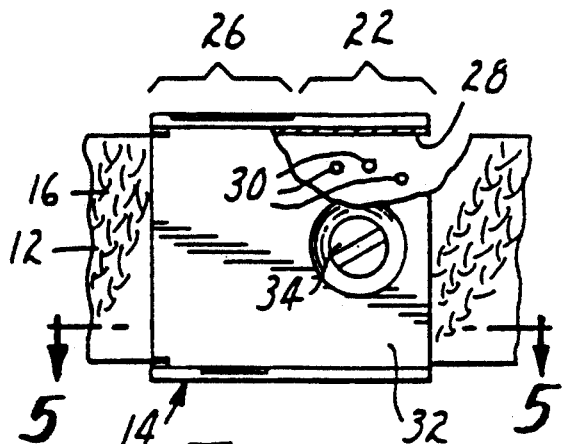
FIG. 4 illustrates a cut-away bottom view of an alternative embodiment of the mechanical connector.
Figure 2:
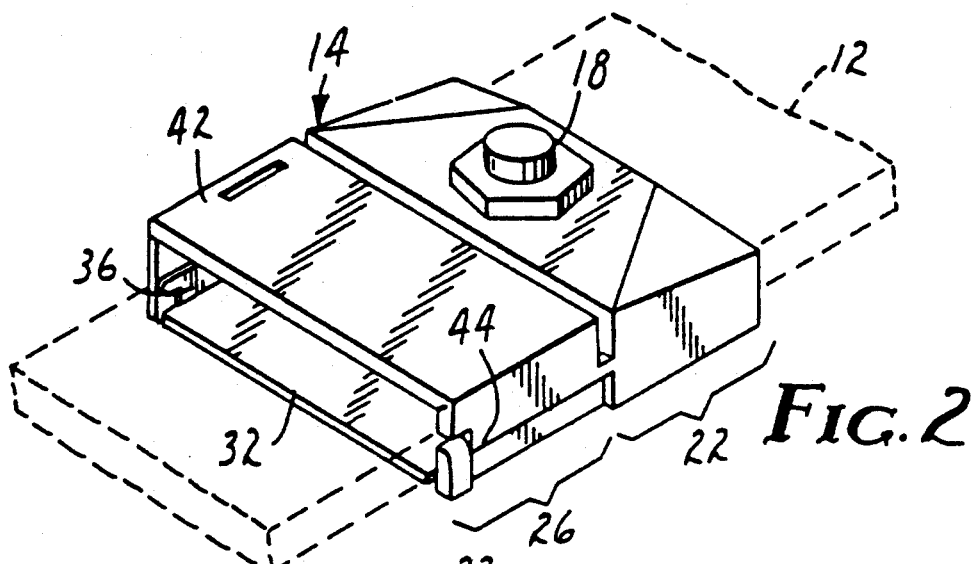
FIG. 2 illustrates a close-up of an alternative mechanical connector of the body strap of FIG. 1 in a closed position.
Figure 3:
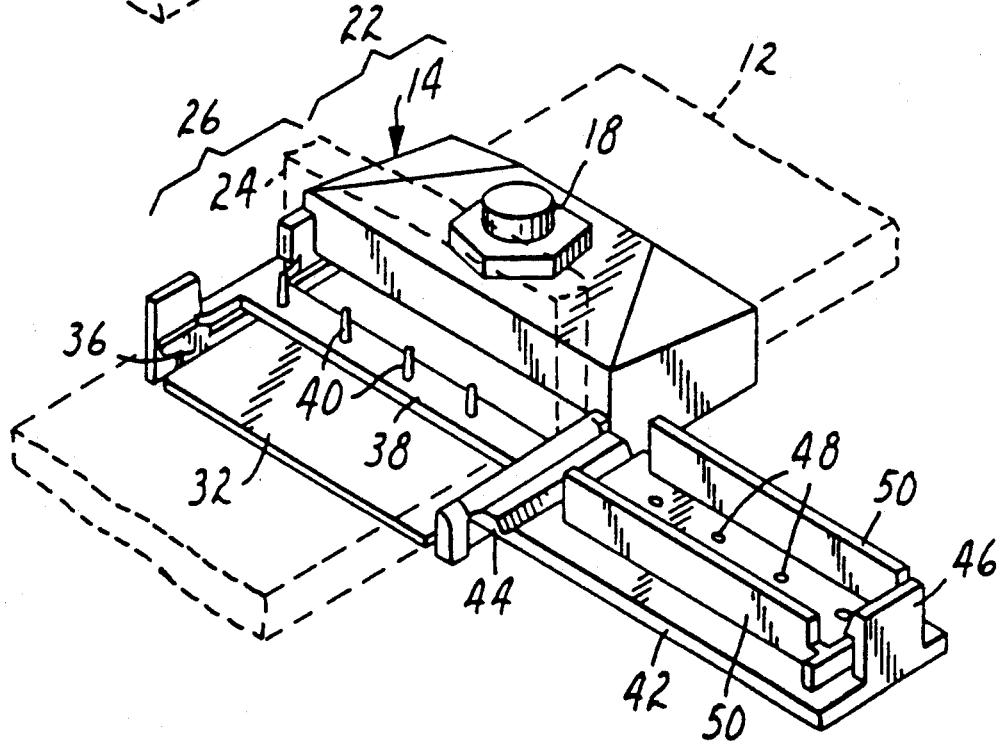
FIG. 3 illustrates a close-up of an alternative embodiment of the mechanical connector in an open position.

The details of connector 14 are more readily illustrated in FIGS. 2 and 3. The first end 20 of the strip of material 12 is secured in the first part 22 of the connector 14. Secured in this manner the first end 20 is semi-permanently secured in that only disassembly of connector 14 can release first end 20 of the strip of material 12 from the connector 14. It is anticipated that body strap 10 can be shipped from the factory with the first end 20 of the strip of material 12 semi-permanently secured in the first part 22 of connector 14. One embodiment of the securing of the first end 20 of the strip of material 12 in the first part 22 of connector 14 is shown in better detail in FIG. 4. The first enc 20 and the strip of material 12 is formed into a recess 28 of the first part 22 of the connector 14. There the strip of material 12 is impaled upon a plurality of spikes 30 designed to secure first end 20 the strip of material 12 within the connector 14 when metallic back plate 32 which is secured in the connector 14 through a stud 34 and its cord connector 18 forming a snap connector. Stud 34 as well as cord connector 18 are metallic allowing for electrical conductivity from the interior surface 16 of the strip of material 12 to cord connector 18 and, of course, subsequently by external cord (not shown) to a ground potential. Metallic back plate 32 also contacts the interior surface 16 of the second end 24 of the strip of material 12 to provide for full 360 degree electrical conductivity around body strap 10.

Again referring to FIGS. 2 and 3, the second end 24 of the strip of material 12 is placed in the recess 36 in the second part 26 of connector 14. The second part 26 of connector 14 contains a transverse bar 38 upon which are mounted a plurality of spikes 40 extending outwardly from the transverse bar 38. The second end 24 of the strip of material 12 is passed under transverse bar 38 and pulled up on the far side of transverse bar 38 until the strip of material 12 is securely tightened around the body part with which it is to be utilized. When the strip of material 12 is suitably tight, the second end 24 of the strip of material 12 is then folded back over the top of transverse bar 38 and impaled upon spikes 40. Hinged cover 42 connected to the second part 26 of connector 14 by hinge 44 along one side, may then be closed over the top of the second end 24 of the strip material 12 and secured with a hook 46 securing hinged cover 42 in place and in turn securing the second end 24 of the strip of material 12 in the connector 14. The second end 24 of the strip of material 12 may be trimmed after the strip of material 12 is impaled upon spikes 40 and either before or after hinged cover 42 is secured in a closed position as illustrated in FIG. 2. Such trimming will prevent the existence of an electrically conductive surface on the exterior of the body strap 10. Hinged cover 42 may contain a plurality of recesses 48 which cooperate with and receive the tips of spikes 40 when hinge cover 42 is in a closed position. The receiving of the tip of spikes 40 in recesses 48 will help prevent spikes 40 from bending, and subsequent release of the strip of material 12 from connector 14.

Figure 5:
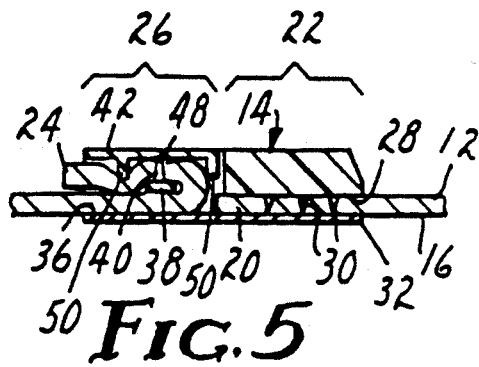
FIG. 5 illustrates a cross-section of an alternative embodiment of the mechanical connector in a closed position.

Hinged cover 42 also may have transverse ridges 50 on one or both sides of transverse bar 38 to force the strip of material 12 into more intimate electrical contact with back plate 32 as is illustrated in the cross-sectional view of FIG. 5. FIG. 5 also illustrates one embodiment of the securing of the first end 20 of the strip of material 12 being impaled upon spikes 30 and the impaling of the second end 24 of the strip of material 12 upon spikes 40 as well as the electrical contact between back plate 32 and both the first end 20 and the second end 24 of the strip of material 12 forming the preferred full 360 degree electrical continuity around body strap 10. FIG. 5 illustrates the second end 24 of the strip of material 12 having been trimmed with a short portion of the second end 24 extending beyond the edge of hinged cover 42. Optionally, the second end 24 of the strip of material 12 will be trimmed at least flush with the edge of hinged cover 42 so that no electrically conductive surface is present on the exterior surface of body strap 10. Also the second end 24 of the strip of material 12 may not be trimmed so short that some material is left to allow for a small amount of unraveling. The material forming connector 14 except for back plate 32, stub 34 and cord connector 18, is constructed from a plastic material, preferably one that is static dissipative. In general, a material is static dissipative if it has a surface resistivity of between $10^8$ and $10^{14}$ ohms per square. Examples of material which could be utilized and which are static dissipative include hygroscopic nylon and carbon loaded polypropylene. As can be seen from examining FIGS. 2, 3 and 5 the second end 24 of the strip of material 12 is secured in connector 14 not only by spikes 40 and hinged cover 42 but also by the tortuous path in which the fabric is forced to take when passed first under and then back over transverse bar 38.

When either the first end 20 or the second end 24 of the strip of material 12 are trimmed particulate from small cut pieces of fibers within the strip of material 12 may come loose from the body strap 10 and contaminate the work place surroundings. This is particularly true of fabric containing a stainless steel fiber as the conductive element in the strip of material 12. Since the stainless steel fiber is actually constructed from a multiplicity of short fibers bundled together to form a continuously conductive long element in the fabric, a trimming of the stainless steel fibers could result in small, conductive fibers being released from the fabric and, hence, the body strap 10. Thus, it is preferred that steps be taken to prevent such contamination. Whether the trimming occurs at the factory, at the site of use, or elsewhere, it is preferred that the end of the strip of material 12 be treated to prevent contamination. The end of the strip of material 12 may be sealed with an adhesive or caulking material. However, it is preferred that the ends of the strip of material 12 be fused. Fusing is a well known process. Typically, fusing results from the application of heat, or the application of heat and pressure in order to melt, or partially melt, at least some of the fibers of the strip of material 12 in order to seal those fibers, and others, within the strip of material 12.

The hinged cover 42 holds the fabric 12 onto spikes 40. Further, transverse ridges 50 assist in holding the fabric 12 onto spikes 40 and help form the tortuous path.

Figure 6:
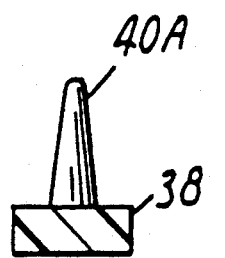
FIG. 6 illustrates one embodiment of the spikes utilized in the embodiment of the mechanical connector illustrated in FIG. 5.
Figure 7:
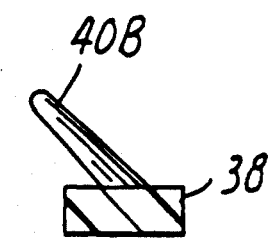
FIG. 7 illustrates another embodiment of the spikes used in the mechanical connector of FIG. 5.
Figure 8:
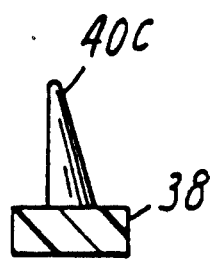
FIG. 8 illustrates another embodiment of the spikes used in the mechanical connector of FIG. 5.

FIGS. 6, 7 and 8 are cross-sections illustrating various optional profiles of spikes 40 taken from a side view. In FIG. 6, spike 40A is of conical shape which is probably the most economical to manufacture and will provide an adequate job of securing strip of material 12 for most purposes. However, severe loading upon spike 40A will tend to lead toward the strip of material 12 rising up toward the end of spike 40A which results in larger lateral forces against spike 40 then otherwise would be encountered. Spike 40C is also of conical shape out has a zero draft, i.e., vertical side, facing the extreme second end 24 of the strip of material 12. Spike 40C with one zero draft side is still economically manufacturable and since the side of the spike 40C which is loaded is vertical strip of material 12 will not tend to ride up toward the tip of the spike 40C and, thus, the lateral force on 40C will not be concentrated at its tip but rather more evenly over the entire length of spike 40C. This results in lower lateral forces on the tip of spike 40 than might otherwise be achieved with spike 40A as illustrated in FIG. 6. If still more lateral loading resistance is desired, then spike 40B as illustrated in FIG. 7 may be utilized. Spike 40B is angled toward the extreme end 24 of strip of material 12, in this case, 45 degrees, so that any lateral force on spike 40B will result in the strip of material 12 being forced more deeply onto to spike 40B and, thus, a more secure environment is provided. However, spike 40B probably is more difficult to manufacture.

Figure 9:
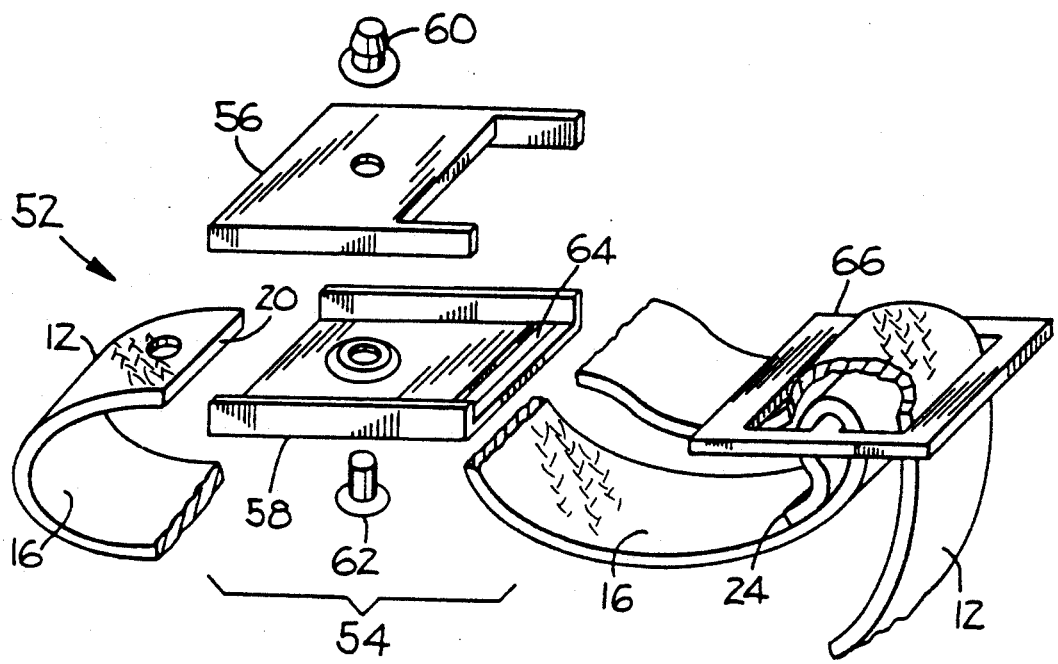
FIG. 9 illustrates an exploded view of an alternative embodiment of the mechanical connector and adjustment mechanism of the adjustable, conductive body strap of the present invention.

While FIGS. 1-8 have illustrated and described adjustable, electrically conductive body straps in general, and have described, in particular, a detailed example of one way in which an adjustable conductive body strap may be constructed, FIG. 9 illustrates another embodiment of an adjustable, conductive body strap 52. A mechanical connector 54 is formed from an outer piece 56 and an inner piece 58. The outer piece 56 and the inner piece 58 are secured together by means of a snap connector 60 and stud 62. Since outer piece 56 is on the exposed exterior surface of the adjustable, conductive body strap 52, outer piece 56 is preferably constructed from an electrically insulative material such as a plastic material, and preferably from nylon or static dissipative plastic. Since inner piece 58 is on the interior surface of the adjustable conductive body strap 52, inner piece 58 is preferably constructed from an electrically conductive material, such as stainless steel or another metal. Inner piece 58 contacts the skin of the wearer and provides an additional electrical contact point from the adjustable conductive body strap 52 to the wearer. The first end 20 of the strip of material 12 is received into one side of mechanical connector 54 from a first direction by a recess formed by the joining of outer piece 56 and inner piece 58. Having been so received the first end 20 of strip of material 12 is held in place mechanically, either by stud 62, by one or more spikes similar to spikes 30 illustrated in FIG. 4 (not shown), both or by other mechanical means. Secured in this manner, the inner conductive surface 16 of the strip of material 12 contacts the electrically conductive inner piece 58. A slot 64 on the other side of inner piece 58 allows for second end 24 of the strip of material to pass, first over and then under inner piece 58 with inner piece 58 making electrical contact with the electrically conductive surface 16 of the strip of material 12. The second end 24 of strip of material 12 is then secured back to itself by an eight-ring 66. Since the eight-ring 66 is exposed to the exterior of the adjustable, conductive body strap 52, it is preferred that it be constructed of an electrically insulative material, again such as a plastic material, preferably nylon or static dissipative plastic. The second end 24 of the strip of material 12 is wrapped around the central member of eight-ring 66 and secured, by any suitable mechanism, such as stitching, to itself firmly securing the second end 24 of the strip of material 12 to the eight-ring 66. The strip of material 12, having been passed between the center leg and the two outer legs of eight-ring 66, then provides a readily readjustable mechanism whereby the user of the adjustable conductive body strap 52 may resize the adjustable conductive body strap 52 in a readily efficient manner. Since there are no free ends of the strip of material 12 exposed following the strip of material 12 being secured in mechanical connector 54, there is no danger of the electrically conductive surface 16 of the strip of material 12 being left exposed to the exterior of the adjustable conductive body strap 52. Snap 60 along with stud 62 form the electrical connection mechanism whereby an electrical ground cable may be connected to snap 60 and the adjustable conductive body strap 52 may be then connected to an electrical ground. Because inner piece 58 is electrically conductive and makes electrical contact to both the first end 20 and the electrically conductive surface 16 of the strip of material 12 near second end 24, dual parallel paths for the drainage of an accumulated electrostatic charge are preferably provided. The adjustable, conductive body strap preferably has full 360 degree electrical continuity and near full 360 degree electrical skin contact. As in the body straps described in FIGS. 1-8, it is preferred that either the first end 20, the second end 24, or both, of the strip of material 12 be fused to prevent contamination.

Figure 10:
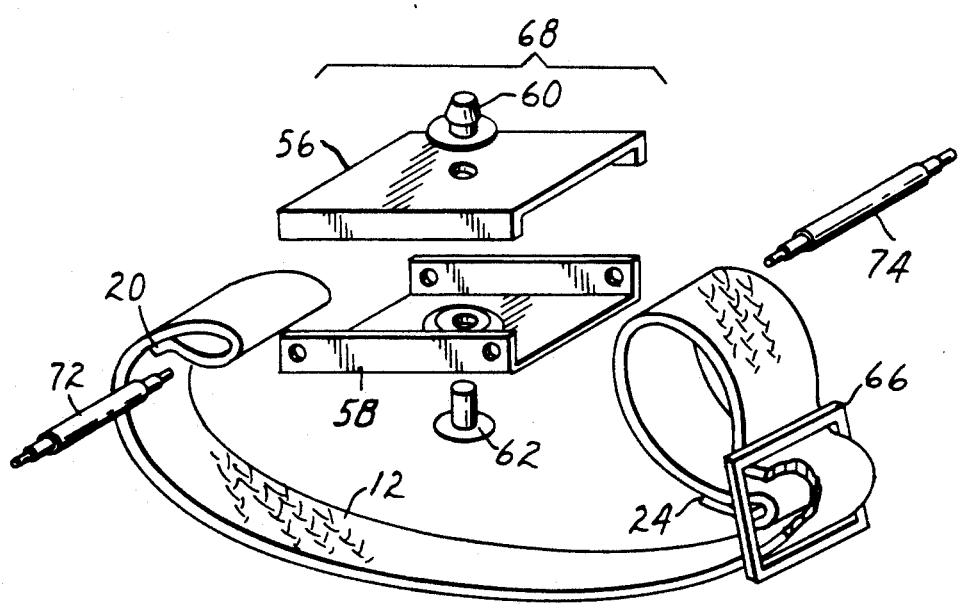
FIG. 10 illustrates an alternative embodiment of the mechanical connector of the body strap of the present invention in which the pins are utilized to secure the ends of the strip of material in place.

FIG. 10 illustrates an alternative embodiment of the adjustable, conductive body strap 10 of the present invention. Body strap 10 of FIG. 10 is similar to the body strap illustrated in FIG. 9 in that connector 68 has an outer piece 56, an inner piece 58, a snap connector 60 with the second end 24 of the strip of material 12 being adjustably held by eight-ring 66. Also similar to the body illustrated in FIG. 9, the first end 20 of the strip of material 12 is secured in the first part 22 of the mechanical connector 68 and the second end 24 of the strip of material 12 passes first around an electrically conductive portion of mechanical connector 68 before being adjustably secured by eight-ring 66. In the mechanical connector 68 the first end 20 of the strip of material 12 is folded back onto itself with the interior surface 16 (the electrically conductive surface) in. There the first end 20 of the strip of material 12 secured to itself such as by fusing the end to the strip of material or by stitching, ultrasonic welding or adhesive. This forms a loop 70 at the first end 20 of the strip of material. Mechanical connector 68 has a bar, or preferably a pin, 72 which may be passed through loop 70 securing the first end 20 of the strip of material 12 in the first part 24 of mechanical connector 68. Preferably, pin 72 is removable from mechanical connector 68 allowing the strip of material 12 to be easily replaced. Pin 72 should be electrically conductive and electrically contact inner piece 58, or otherwise provide electrical connection between pin 72 and snap connector 60. The second part 26 of mechanical connector 68 is constructed with a similar bar, or preferably a pin 74. Pin 74 may be passed through the loop formed of the second end 24 of the strip of material 12 when the strip of material is looped back to be adjustably secured in eight-ring 66. Thus, pin 74 substitutes for the slot 64 in the inner piece 58 of mechanical connector 54 illustrated in FIG. 9. Again preferably, pin 74 is removable from mechanical connector 68 allowing the strip of material 12 to be easily replaced. Pin 74 should be electrically conductive and electrically contact inner piece 58, or otherwise provide electrical connection between pin 74 and snap connector 60. Pins 72 and 74 (after being passed through the loop formed in the strip of material 12) are inserted into recesses in inner piece 58. Pins 72 and 74 preferably are spring loaded enabling them to snap into and be secured in outer piece 56 without further adjustment. Pins 72 and 74 are electrically conductive allowing an electrical connection between the interior surface 16 of the strip of material 12 and the electrically conductive inner piece 58. Inner piece 58 is then secured to outer piece 56 by snap connector 60 and stud 62.

Figure 11:
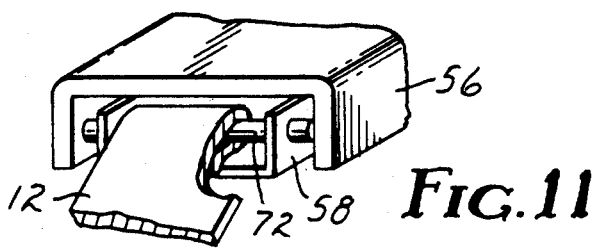
FIG. 11 illustrates an alternative detail embodiment of the pins utilized in the mechanical connector of FIG. 10.

FIG. 11 illustrates an alternative embodiment for the pins 72 and 74 and their connection to the remaining portions of the mechanical connector 68. Pins 72 and 74 are inserted through the loop formed in the strip of material 12. Pins 72 and 74 then pass through holes in inner piece 58 and are fitted into securing recesses in outer piece 56. Pins 72 and 74 preferably are spring loaded enabling them to snap into and be secured in outer piece 56 without further adjustment. Again pins 72 and 74 are electrically conductive allowing an electrical connection between the interior surface 16 of the strip of material 12 and the electrically conductive inner piece 58.

Figure 12:
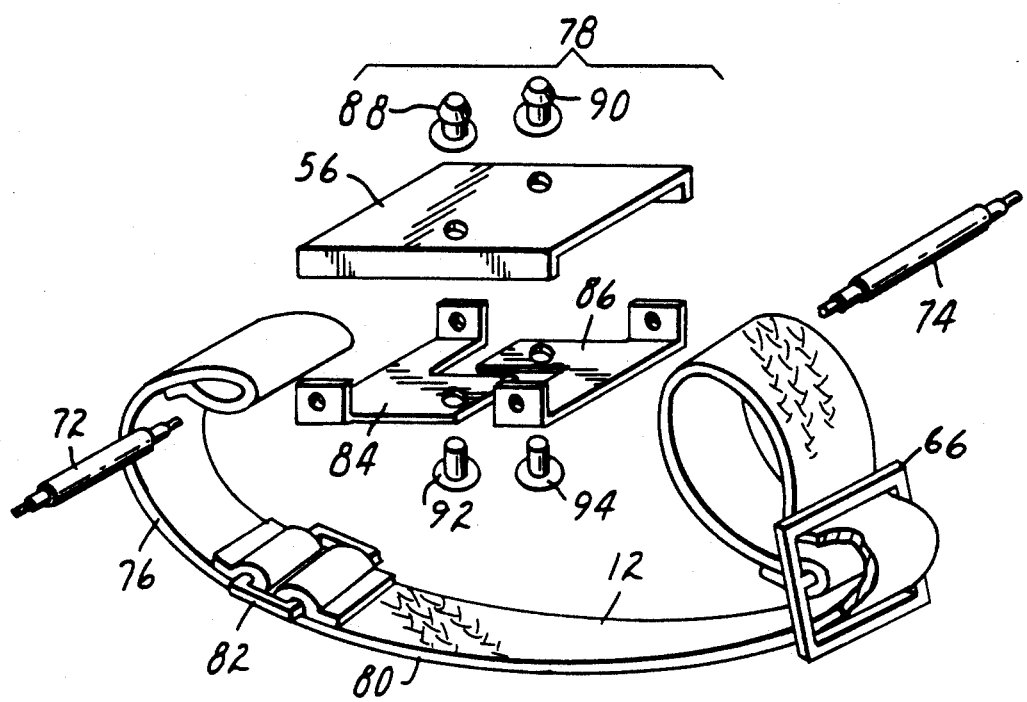
FIGS. 12 and 13 illustrate alternative embodiments of body straps similar to the body strap illustrated in FIG. 10 out which each have dual conductive paths.
Figure 13:
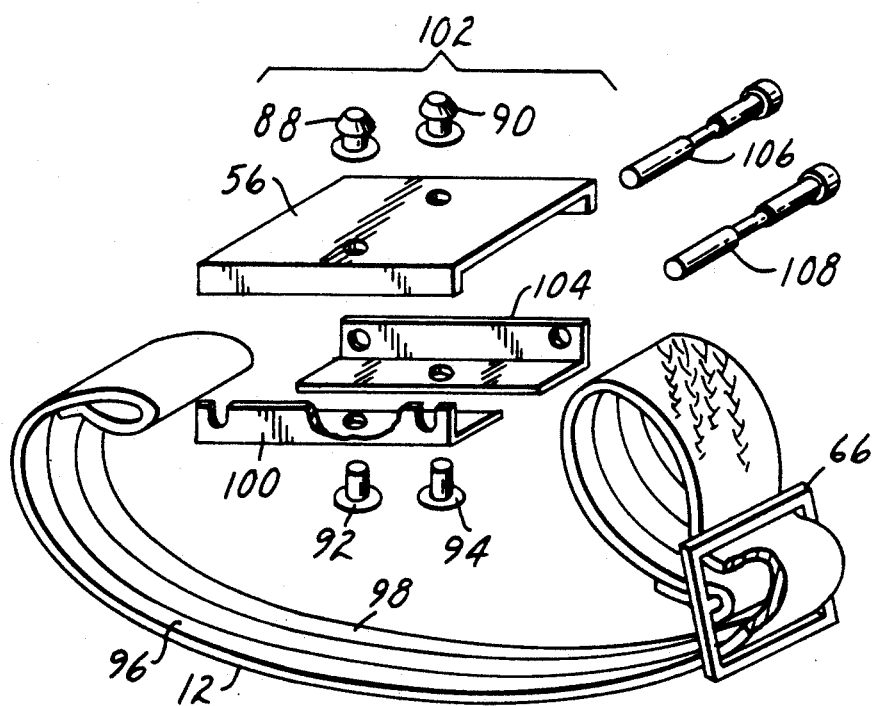

Sometimes it is desirable to have a body strap 10 with a plurality of conductive paths. Such body straps are useful in conjunction with commercially available body strap monitors. FIGS. 12 and 13 illustrate body straps similar to the body strap of FIG. 10 but which have dual conductive paths.

In the body strap 10 of FIG. 12 the strip of material 12 is divided into two portions, a first portion 76 toward the first end 20 directly coupled to the first part of the mechanical connector 78 and a second portion 80 toward the second end 24 directly coupled to the second part of the mechanical connector 78. The first end 20 of the strip of material 12 is coupled to the mechanical connector 78 as is shown in FIG. 10. Similarly the second end 24 of the strip of material 12 is coupled to the mechanical connector 78 as is shown in FIG. 10. The first portion 76 and the second portion 80 of the strip of material 12 are physically coupled in an insulated coupler 82. So coupled the first portion 76 and second portion 80 are physically connected but electrically separated. The inner piece 58 of the mechanical connector 68 of FIG. 10 is replaced by a split inner piece having a first part 84 and a second part 86. Both the first part 84 and the second part 86 of the inner piece are electrically conductive. The first part 84 receives the first portion 76 of the strip of material 12 with pin 72. The second part 86 receives the second portion 80 of the strip of material 12 with pin 74. Thus the first portion 76 of the strip of material 12 is electrically connected to the first part 84 of the inner piece of the mechanical connector 78 and the second portion 80 of the strip of material is electrically connected to the second part 86 of the inner piece of the mechanical connector 78. The first 84 and second 86 parts of the inner piece are arranged so that they do not contact each other, thus keeping the electrical circuits of the two portions separate. Alternatively, the first 84 and second 86 parts could be allowed to contact each other physically but insulators could be used to keep the parts electrically isolated. In the embodiment shown in FIG. 12, the first part 84 and the second part 86 of the inner piece are separately coupled to outer piece 56 with snap connectors 88 and 90, respectively, and studs 92 and 94, respectively. Alternatively, a single snap connector could be utilized which contained dual electrical contacts with only one contact being electrically coupled to the first part 84 and, correspondingly, to the second part 86 of the inner piece of the mechanical connector.

In the body strap 10 of FIG. 13 the strip of material 12 is physically one continuous strip but is divided into dual parallel electrical paths 96 and 98. The first electrical path 96 is directly coupled to the first part 100 of the inner piece of the mechanical connector 102. The second electrical path 98 is directly coupled to the second part 104 of the inner piece of the mechanical connector 102. The first part 100 and the second part 104 of the inner piece each are arranged to couple to both ends of the strip of material 12. The first part 100 and the second part 104 of the inner piece, however, are electrically separated longitudinally so that the dual electrical paths 96 and 98 remain electrically isolated. Pins 106 and 108, receiving the first end 20 and the second end 24 of the strip of material 12 respectively, are both electrically conductive but also have dual electrical elements. The pins 106 and 108 are electrically conducted on each end which are electrically separate as with an insulated spacer. Thus the first electrical path 96 of the strip of material 12 is electrically connected to snap connector 88 of the mechanical connector 102 and the second electrical path 98 of the strip of material is electrically connected to snap connector 90 of the mechanical connector 102. The first 100 and second 104 parts of the inner piece are arranged so that they do not contact each other, thus keeping the electrical circuits of the two portions separate. Alternatively, the first 100 and second 104 parts could be allowed to contact each other physically but insulators could be used to keep the parts electrically isolated. In the embodiment shown in FIG. 13, the first part 100 and the second part 104 of the inner piece are separately coupled to outer piece 56 with snap connectors 88 and 90, respectively, and studs 92 and 94, respectively. Alternatively, a single snap connector could be utilized which contained dual electrical contacts with only one contact being electrically coupled to the first part 100 and, correspondingly, to the second part 104 of the inner piece of the mechanical connector.

In the body straps illustrated in FIGS. 10-13, it is preferred that the first end 20, the second end 24, or both, of the strip of material 12 to be fused in order to prevent contamination.

Thus, it can be seen that there has been shown and described a novel adjustable, conductive body strap. It is to be recognized and understood, however, that various changes, modifications and substitution in the form and of the details of the present invention may be made by those skilled in the art without departing from the scope of the following claims.

What is claimed is:

1. An adjustable, conductive body strap, comprising:
   a strip of material having a first end and a second end, said strip of material being electrically conductive on at least one surface, being elastomerically extensible in its longitudinal direction, and being of at least a length to enable said strip of material to encircle a body part;
   an electrically insulative outer piece;
   an electrically conductive inner piece;
   said outer piece and said inner piece being secured together to form a mechanical connector receiving said first end and said second end of said strip of material to form a closed loop with said strip of material and with said at least one surface toward the interior of said closed loop;
   said mechanical connector receiving said first end of said strip of material from a first direction with said first end of said strip of material being secured therein, said electrically conductive inner piece making electrical contact with said at least one surface at said first end of said strip of material;
   said electrically conductive inner piece having a portion around which said second end of said strip of material is passed, said electrically conductive inner piece making electrical contact with said at least one surface of said strip of material wherein said strip of material passes around said portion providing 360 degree electrical continuity;
   adjustment means secured to said second end of said strip of material and to said strip of material intermediate said mechanical connector for adjustably holding said strip of material in said closed loop; and
   electrical connection means coupled to said strip of material for making electrical contact with said at least one conductive surface and for providing a connection point for an electrical cable capable of connecting said conductive body strap to ground;

2. An adjustable, conductive body strap as in claim 1 wherein said inner piece of said mechanical connector is a metallic plate and is secured by means of a metallic stud formed to receive a snap connector, said metallic plate and metallic stud forming said electrical connection means.

3. An adjustable, conductive body strap, comprising:
   a strip of material having a first end and a second end, said strip of material being electrically conductive on at least one surface, being elastomerically extensible in its longitudinal direction, and being of at least a length to enable said strip of material to encircle a body part;
   a mechanical connector receiving said first end and said second end of said strip of material to form a closed loop with said strip of material with said at least one surface toward the interior of said closed loop, said mechanical connector having a first part receiving said first end of said strip of material from a first direction with said first end of said strip of material being secured therein and having a second part receiving said second end of said strip of material;
   said second part of said mechanical connector having a plate over which said second end of said strip of material is passed, said plate having a plurality of spikes upon which said strip of material may be impaled after said strip of material has been pulled tight around said body part, said second part of said mechanical connector further having a hinged cover for being secured over said spikes of said plate trapping said strip of material thereon, said hinged cover being hingably attached at one side of said mechanical connector so that said hinged cover can be closed transversely across said strip of material;
   a second cover secured to said first part of said mechanical connector; and electrical connection means coupled to said strip of material for making electrical contact with said at least one conductive surface and for providing a connection point for an electrical cable capable of connecting said conductive body strap to ground.

4. An adjustable, conductive body strap as in claim 3 wherein said second cover is electrically conductive on its side which faces said strip of material and wherein said second cover makes electrical contact with said at least one surface of said strip of material.

5. An adjustable, conductive body strap, comprising:
a strip of material having a first end and a second end, said strip of material being electrically conductive on at least one surface, being elastomerically extensible in its longitudinal direction, and being of at least a length to enable said strip of material to encircle a body part;
a mechanical connector receiving said first end and said second end of said strip of material to form a closed loop with said strip of material with said at least one surface toward the interior of said closed loop, said mechanical connector having a first part receiving said first end of said strip of material from a first direction with said first end of said strip of material being secured therein and having a second part receiving said second end of said strip of material;
said second part of said mechanical connector having a transverse bar around which said second end of said strip of material is passed firstly interior of said transverse bar and secondly exterior of aid transverse bar, said transverse bar having a plurality of spikes mounted on its exterior surface upon which said strip of material may be impaled after said strip of material has been pulled tight around said body part, said second part of said mechanical connector further having a hinged cover for being secured over said spikes of said plate trapping said strip of material thereon, said hinged cover being hingably attached at one side of said mechanical connector so that said hinged cover can be closed transversely across said strip of material; and
electrical connection means coupled to said strip of material for making electrical contact with said at least one conductive surface and for providing a connection point for an electrical cable capable of connecting said conductive body strap to ground.

* * * * *

UNITED STATES PATENT AND TRADEMARK OFFICE
CERTIFICATE OF CORRECTION

PATENT NO. : 5,134,538
DATED : July 28, 1992
INVENTOR(S) : John W. Weiss

It is certified that error appears in the above-identified patent and that said Letters Patent is hereby corrected as shown below:

```
Col. 5, Line 45, "out" should read --but--.
Col. 6, Line 25, "enc" should read --end--.
Col. 7, Line 26, "stub" should read --stud--.
Col. 8, Line 8, "out" should read --but--.
Col. 12, Line 17, "wherein" should read --where--.
Col. 12, Line 29, "ground" should be followed by --said
adjustment means being an eight-ring.--

Col. 12, Line 7, "aid" should read --said--.
```

Signed and Sealed this

Thirtieth Day of November, 1993

Attest:

BRUCE LEHMAN

Attesting Officer

Commissioner of Patents and Trademarks